US 6,720,356 B2

(12) United States Patent
Feldman

(10) Patent No.: US 6,720,356 B2
(45) Date of Patent: Apr. 13, 2004

(54) MAGNESIUM DI-POTASSIUM EDTA COMPLEX AND METHOD OF ADMINISTRATION

(76) Inventor: Spencer Feldman, 2599A, Makawao, HI (US) 96768

( * ) Notice: Subject to any disclaimer, the term of this patent is extended or adjusted under 35 U.S.C. 154(b) by 0 days.

(21) Appl. No.: 10/124,763

(22) Filed: Apr. 19, 2002

(65) Prior Publication Data

US 2002/0169211 A1 Nov. 14, 2002

Related U.S. Application Data

(60) Provisional application No. 60/285,546, filed on Apr. 20, 2001.

(51) Int. Cl.$^7$ ................ A61K 31/195; A61K 38/16; A61K 9/70
(52) U.S. Cl. ................ 514/566; 514/561; 514/578; 424/449
(58) Field of Search ................ 514/566, 578, 514/561; 424/449

(56) References Cited

U.S. PATENT DOCUMENTS

| | | | | |
|---|---|---|---|---|
| 2,781,291 A | * | 2/1957 | Rubin et al. ................ 514/566 |
| 3,184,381 A | * | 5/1965 | Ashmead et al. ........ 424/78.22 |
| 3,838,196 A | * | 9/1974 | Mercer et al. .............. 514/566 |
| 4,196,196 A | * | 4/1980 | Tiholiz ........................... 514/4 |
| 4,344,940 A | * | 8/1982 | Chow et al. ................ 514/174 |
| 4,372,858 A | * | 2/1983 | Ritter ........................ 210/674 |
| 5,114,974 A | | 5/1992 | Rubin ........................ 514/566 |
| 5,155,096 A | * | 10/1992 | Garcia y Bellon et al. ..... 514/3 |
| 5,602,180 A | | 2/1997 | Bennett ..................... 514/578 |
| 6,114,387 A | | 9/2000 | Cutler ........................ 514/562 |

OTHER PUBLICATIONS

"Oral Chelation and Nutritional Replacement Therapy for Chemical & Heavy Toxicity and Cardiovascular Disease", Maile Pouls Townsend Letter, 1999.*

* cited by examiner

Primary Examiner—Zohreh Fay
Assistant Examiner—Brian Yong S Kwon
(74) Attorney, Agent, or Firm—Darby & Darby

(57) ABSTRACT

A composition containing an EDTA complex in the form of a suppository is provided. More specifically, the EDTA complex is a magnesium di-potassium EDTA complex. The suppository may contain a controlled release agent which will release the EDTA complex over a period of several hours.

3 Claims, No Drawings

MAGNESIUM DI-POTASSIUM EDTA COMPLEX AND METHOD OF ADMINISTRATION

This application claims priority under 35 U.S.C. §119 from provisional patent application Ser. No. 60/285,546, filed Apr. 20, 2001, which is hereby incorporated by reference in its entirety.

FIELD OF THE INVENTION

The present invention relates to a composition containing a chelating agent, more particularly to an EDTA complex to be administered in suppository form.

BACKGROUND OF THE INVENTION

Chelating agents are well known organic compounds that are capable of forming complexes of multivalent metal ions. Chelation therapy, involving the administration of EDTA (ethylene diamine tetraacetic acid) complexes for removing arterial calcium plaque, or for removing heavy metals such as lead has been extensively employed. For example, EDTA has been used to remove high levels of lead from the bloodstream of those who have been exposed to lead paint. Intravenous injection of chelators has been widely used for the treatment of atherosclerosis. Intravenous administration may take several hours per session, and several sessions per month for many months. Such a treatment schedule is inconvenient to the patient and health care provider.

Oral chelation therapy is also well known as a more convenient method. However, when administered orally, a very low percentage of the EDTA complex is actually absorbed by the bloodstream.

It is known that EDTA may be administered in a suppository form. Bennett U.S. Pat. No. 5,602,180 relates to a method of administering a disodium EDTA complex in the form of a controlled release suppository. U.S. Pat. No. 5,602,180 is hereby incorporated into this specification by reference.

Disodium EDTA has the disadvantage of raising sodium levels. Sodium stimulates the sympathetic system, causing, among other effects, an increase in blood pressure, pulse pressure, and heart rate. These affects are undesirable in the patient suffering from atherosclerosis, a condition for which EDTA therapy is often prescribed. As sodium increases pulse pressure, the amplitude of the cyclic changes in lumen size and shape are increased. These cyclic changes may lead to the disruption of plaque and subsequent myocardial infarction. See Valentin Fuster, MD, "The Vulnerable Atherosclerotic Plaque" (American Heart Association).

SUMMARY OF THE INVENTION

The present invention provides an alternative to the intravenous injection or oral formulation of EDTA chelating agents. A method of administering EDTA complexes includes forming a suppository containing a magnesium di-potassium EDTA complex. The suppository may also contain a controlled-release agent, which, when used, will release the complex over a period of several hours.

DETAILED DESCRIPTION OF THE INVENTION

According to this invention, a suppository is formed of magnesium di-potassium EDTA complex and a matrix, which may or may not contain a time release agent. The magnesium di-potassium EDTA complex may be obtained from Fluka of Switzerland as EDTA dipotassium magnesium salt monohydrate or EDTA dipotassium magnesium salt (product No. 40694). It can also be in the anhydrous form. The suppository is molded in a common shape from a waxy material in which the active ingredients have been dissolved or suspended. The base material may comprise cocoa butter, glycerin, glyceryl, monopalmitate, glyceryl monostearate, hydrogenated coconut oil fatty acids and hydrogenated palm kernel oil fatty acids or polyethylene glycol. The choice of base material is a matter of ordinary skill.

Methods of making controlled release suppositories are well known. Choosing suitable carrier materials, and suitable matrix ingredients, are within the skill of the artisan in this field. Representative prior U.S. patents include U.S. Pat. Nos. 4,265,875, 4,292,300, 4,406,883, 5,151,434, 5,188,840, 5,215,758, 5,352,455, and 5,393,528. The foregoing patents are hereby incorporated into this specification by reference. The release-controlling agents, and their concentrations, should be chosen so that release occurs within the body over a one to four hour period after the suppository is administered.

In addition to avoiding the above mentioned disadvantages of disodium EDTA, the invention provides other advantages as well. Magnesium suppresses the sympathetic system and potassium stimulates the parasympathetic system. Thus the complex of the present invention may lower blood pressure, pulse and coronary blood flow. The magnesium di-potassium EDTA complex can also be used as a form of magnesium or potassium supplementation.

A magnesium di-potassium EDTA complex as described can also be administered orally to supplement magnesium and potassium levels. The complex also can be administered orally to treat arterial plaque and heavy metal toxicity.

I claim:

1. A method of administering a magnesium di-potassium EDTA complex to a patient, comprising the steps of:
   (a) forming a suppository consisting essentially of containing magnesium di-potassium EDTA and
   (b) administering said suppository to the patient.
2. The method of claim 1, wherein the suppository contains controlled release agents which release the magnesium di-potassium EDTA over a period of about one to four hours after placement in the anus.
3. The method of claim 1 wherein the suppository is administered vaginally.

* * * * *